(12) United States Patent
Jang

(10) Patent No.: US 8,636,671 B2
(45) Date of Patent: Jan. 28, 2014

(54) WEARABLE RESPIRATION MEASUREMENT APPARATUS

(75) Inventor: Yong Won Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 259 days.

(21) Appl. No.: 12/878,857

(22) Filed: Sep. 9, 2010

(65) Prior Publication Data

US 2011/0152707 A1    Jun. 23, 2011

(30) Foreign Application Priority Data

Dec. 21, 2009    (KR) ........................ 10-2009-0128371

(51) Int. Cl.
*A61B 5/08*    (2006.01)

(52) U.S. Cl.
USPC .......................................... 600/539; 600/538

(58) Field of Classification Search
None
See application file for complete search history.

(56) References Cited

U.S. PATENT DOCUMENTS

| | | | |
|---|---|---|---|
| 5,704,366 A |   | 1/1998 | Tacklind et al. |
| 5,732,709 A | * | 3/1998 | Tacklind et al. ............. 600/539 |
| 6,126,613 A | * | 10/2000 | Edwards et al. ............. 600/539 |
| 2006/0270941 A1 |   | 11/2006 | Xie et al. |
| 2008/0221470 A1 |   | 9/2008 | Sather |

FOREIGN PATENT DOCUMENTS

| | | | |
|---|---|---|---|
| DE | 1342370 | * | 1/1971 |
| GB | 1342370 |   | 1/1974 |
| JP | 03-261484 A |   | 11/1991 |
| JP | 2004-275690 A |   | 10/2004 |
| JP | 2005-95647 A |   | 4/2005 |
| JP | 2005-137479 A |   | 6/2005 |
| JP | 2005-160644 A |   | 6/2005 |
| JP | 2007-512876 |   | 5/2007 |
| JP | 2010-137033 A |   | 6/2010 |
| KR | 19960004081 |   | 5/1996 |
| KR | 1020020022966 | * | 4/2002 |
| KR | 1020020035554 A |   | 5/2002 |
| KR | 10-0828132 B1 |   | 5/2008 |
| WO | WO 2005/053542 A1 |   | 6/2005 |

OTHER PUBLICATIONS

Kiyoshi Hoshino, "Long-term Measurements and Analyses of Human Nasal Cycle", 2002, pp. 1841-1844, vol. 56, No. 11, Japan.
Kiyoshi Hoshino, "Application of multivariate autoregressive modeling for the nasal cycle", The 33$^{rd}$ Annual Conference of the IEEE Industrial Electronics Society (IECON), Nov. 5-8, 2007, pp. 2537-2541, IEEE.
K. Hoshino et al., "Long-term Measurements and Analyses of Human Nasal Cycle", Technical Report of IEICE (HIP2003-41), Jul. 2003, pp. 69-72, vol. 103, No. 166, The Institute of Electronics, Information and Communication Engineers.

\* cited by examiner

*Primary Examiner* — Michael Kahelin
*Assistant Examiner* — Mitchell Alter

(57) ABSTRACT

A wearable respiration measurement apparatus including: an eyeglass frame having a nose flap which is formed in such a manner as to cover a user's nose; and an induced current generation device attached to the nose flap and generating an induced current corresponding to an amount of air inhaled or exhaled through the user's nose.

17 Claims, 5 Drawing Sheets

WEARABLE RESPIRATION MEASUREMENT APPARATUS

CROSS-REFERENCE TO RELATED APPLICATIONS

This application claims the priority of Korean Patent Application No. 10-2009-0128371 filed on Dec. 21, 2009, in the Korean Intellectual Property Office, the disclosure of which is incorporated herein by reference.

BACKGROUND OF THE INVENTION

1. Field of the Invention

The present invention relates to a wearable respiration measurement apparatus, and more particularly, to a wearable respiration measurement apparatus which is implemented in the form of eyeglasses and is capable of precisely acquiring respiration-related information, while minimizing behavioral limitations on a user.

2. Description of the Related Art

As the concept of ubiquitous healthcare has been introduced, necessary measurements may be carried out anytime and anytime. With such convenience, much development has been accomplished in the emerging field of ubiquitous healthcare in the area of measuring and managing people's health.

Although a great deal of development has been accomplished in various health care fields, a method for measuring respiration precisely and easily has not yet been proposed.

Research has been conducted into a method for measuring a respiration amount by using a band worn on a user's chest, which includes a piezoelectric element, or using the Doppler effect caused by a radar or the like. However, this method has a disadvantage in that it has low precision in terms of the measurement of respiration amount.

in particular, since it is difficult to reduce an error for body motions, there are many difficulties in precisely measuring a respiration amount without imposing behavioral limitations on a user while the user is exercising, for example, Jogging.

SUMMARY OF THE INVENTION

An aspect of the present invention provides a wearable respiration measurement apparatus which is implemented in the form of eyeglasses and capable of acquiring respiration-related information more precisely, while minimizing behavioral limitations on a user.

According to an aspect of the present invention, there is provided a wearable respiration measurement apparatus including: an eyeglass frame having a nose flap which is formed in such a manner as to cover a user's nose; and an induced current generation device attached to the nose flap and generating an induced current corresponding to an amount of air inhaled or exhaled through the user's nose.

The induced current generation device may include: a body having an inhalation path formed therein; a propeller installed inside the inhalation path so as to be rotated by air inhaled through the inhalation path; and a plurality of coils installed on the inner surface of the inhalation path and generating an induced current along alternate magnetic fields caused by the rotation of the propeller.

The propeller may include a plurality of blades having a magnetic property, among which odd-numbered blades have an opposite magnetic polarity to even-numbered blades.

The odd-numbered coils among the plurality of coils may have an opposite polarity to the even-numbered coils. The plurality of coils may be connected in parallel to each other.

The body may include: the inhalation path; an exhalation path housed within the inhalation path; an inhalation valve plate installed in the inhalation path and opened only during inhalation; an exhalation valve plate installed in the exhalation path and opened only during exhalation; and a frame fixing the inhalation path to the inside of the exhalation path and supporting the position of the propeller.

The inhalation valve plate may be installed at a lower position than the exhalation valve plate.

The nose flap may be implemented in such a manner as to cover only the nose or cover both the nose and the mouth.

The wearable respiration measurement apparatus may further include a mouthpiece for inducing respiration through the nose, when the nose flap is implemented in such a manner as to cover only the nose. The mouthpiece may be implemented in such a manner as to be separated from the eyeglass frame. Alternatively, the wearable respiration measurement apparatus may further include a mouthpiece for inducing respiration through the nose, when the nose flap is implemented in such a manner as to cover both the nose and the mouth. The mouthpiece is attached to the eyeglass frame so as to be positioned under the nose flap. The mouthpiece may include a temperature sensor mounted thereon.

The wearable respiration measurement apparatus may further include a signal processing device attached to, or inserted into, the eyeglass frame and generating respiration-related information corresponding to the induced current. The signal processing device may include: a current-voltage converter converting the induced current into a voltage; a filter removing noise contained in the voltage; an amplifier amplifying the voltage from which the noise is removed; an analog-digital converter generating a digital signal corresponding to the amplified voltage; a controller analyzing the generation pattern of the digital signal to calculate information on one or more of the respiration rate and the respiration amount, a memory storing an output of the controller; an external interface providing the output of the controller or the information stored in the memory to an external device through a wired or wireless communication scheme; and a power supply unit providing power required for driving the signal processing device.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
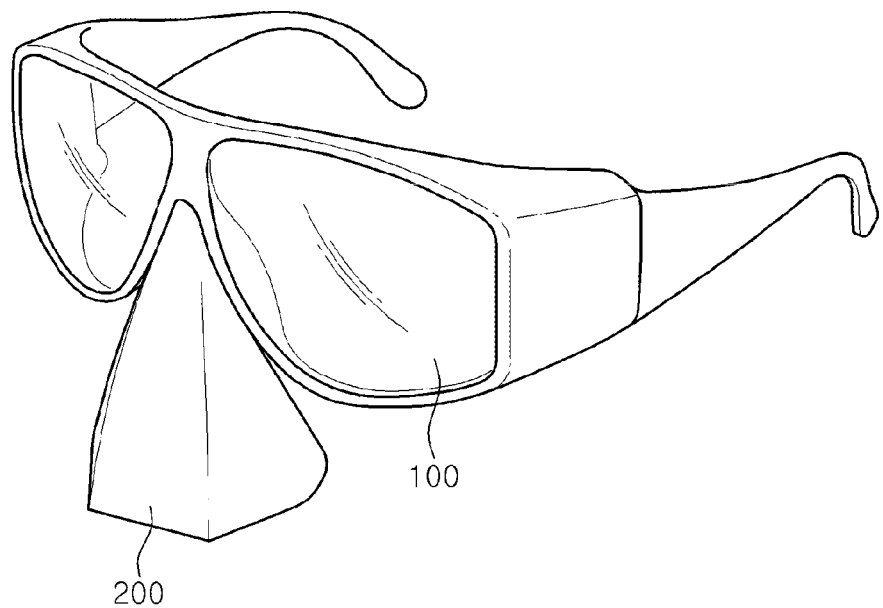
FIG. 1 is a perspective view illustrating the exterior of a wearable respiration apparatus according to an embodiment of the present invention.

Exemplary embodiments of the present invention will now be described in detail with reference to the accompanying drablades. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the thicknesses of layers and regions are exaggerated for clarity. Like reference numerals in the drablades denote like elements, and thus their description will be omitted.

Furthermore, when it is described that one component 'includes' another component, it means that the one component does not exclude yet another component, but may include yet another component.

Figure 2:
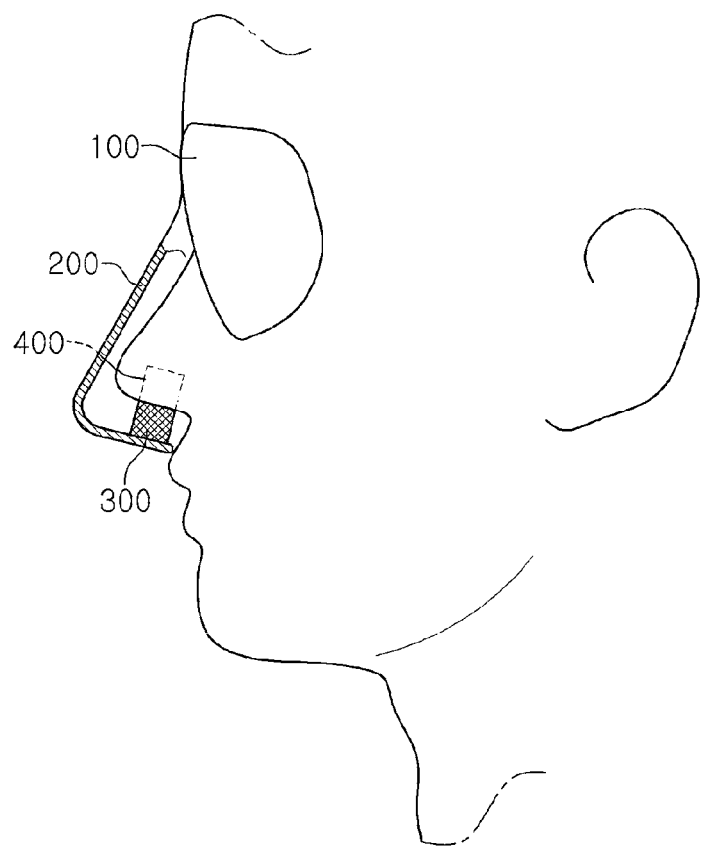
FIG. 2 is a cross-sectional view illustrating the wearable respiration apparatus according to the embodiment of the present invention.
Figure 3:
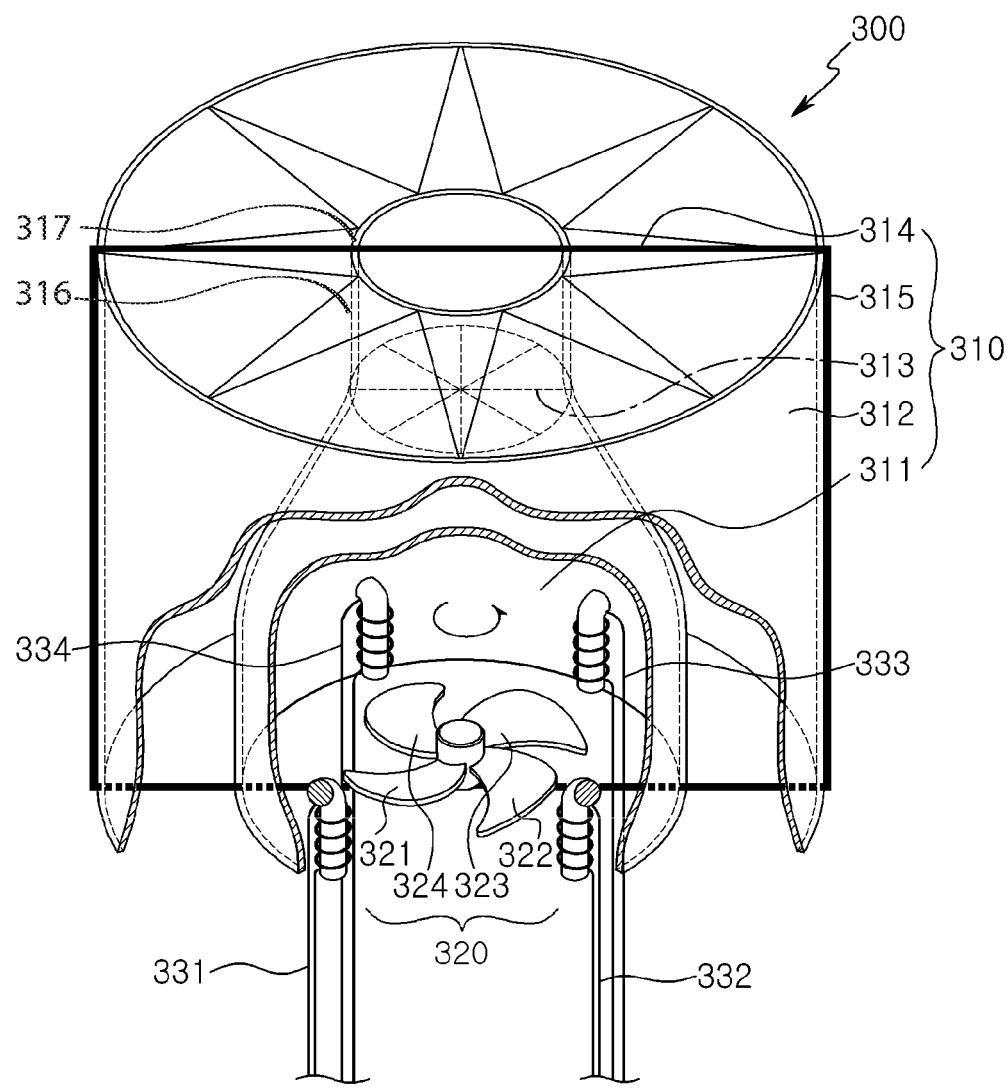
FIG. 3 is a partially cut-away view of an induced current generation device according to the embodiment of the present invention.

FIGS. 1 to 3 are diagrams illustrating the exterior of a wearable respiration measurement apparatus according to an embodiment of the present invention.

Referring to FIGS. 1 and 2, the wearable respiration measurement apparatus according to the embodiment of the present invention includes an eyeglass frame 200 and an induced current generation device 300. The eyeglass frame 100 includes a nose flap 200 which is formed in such a manner as to cover a person's nose. The induced current generation device 300 is attached to inside of the nose flap 200 and generates an induced current corresponding to an amount of air which is inhaled into or exhaled from the person's nose.

Referring to FIG. 3, the induced current generation device 300 has a body 310. The body 310 includes an inhalation path 311, an exhalation path 312 having the inhalation path 311 housed therein, an inhalation valve plate 313 which is installed in the inhalation path 311 and opened only during inhalation, an exhalation valve plate 314 which is installed in the exhalation path 312 and opened only during exhalation, and a frame 315 which fixes the inhalation path 311 to the inside of the exhalation path 312 and supports the position of a propeller 320. A path 316 extends from the inhalation valve plate 313 to the exhalation valve plate 314 to form a hole 317 in the exhalation valve plate 314.

During exhalation, the exhalation valve plate 314 may be humidified by the moisture of the exhaled air. Therefore, the inhalation valve plate 313 may be positioned under the exhalation valve plate 314 such that dry air may pass through the hole 317 of the exhalation valve plate 314.

The induced current generation device 300 further includes the propeller 320 and a plurality of coils 331 to 334. The propeller 320 is installed in the inhalation path 311 so as to be rotated by air inhaled through the inhalation path 311. The plurality of coils 331 to 334 are installed in the inner surface of the inhalation path 311 so as to generate induced currents along alternate magnetic fields caused by the rotation of the propeller 320.

The propeller 320 includes a plurality of blades 321 to 324, each having a magnetic property. Among the plurality of blades 321 to 324, odd-numbered blades 321 and 323 may have an opposite magnetic polarity to even-numbered blades 322 and 324. For example, when it is assumed that the propeller 320 includes four blades numbered 1 through 4, the blades numbered 2 and 4 may have an N pole, and the blades numbered 1 and 3 may have an S pole.

Similarly, among the plurality of coils 331 to 334, the odd-numbered coils 331 and 333 may have an opposite polarity to the even-numbered coils 332 and 334. For example, when it is assumed that the induced current generation device 300 includes four coils numbered 1 through 4, the coils numbered 1 and 3 may be wound in the same direction, and the coils numbered 2 and 4 may be wounded in the same direction. In other words, the coils numbered 1 and 3 may be wound in a different direction from the coils numbered 2 and 4.

When the magnetic properties of the propeller 320 and the polarities of the coils 331 to 334 are set in such a manner, it is possible to maximize the current induced through the coils 331 to 334 by the rotation of the propeller.

Figure 4:
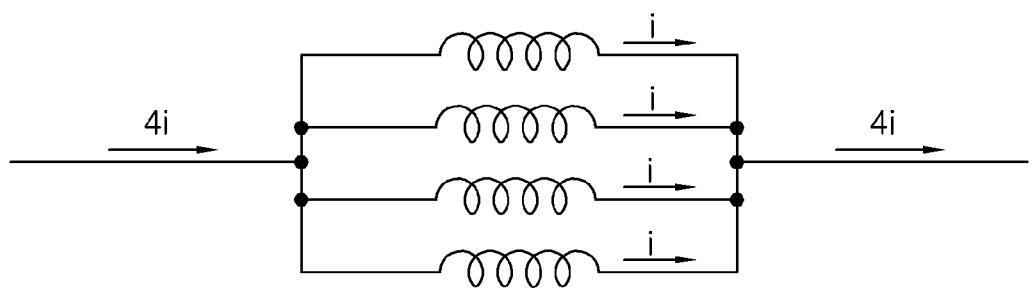
FIG. 4 is a diagram illustrating the connection structure of a plurality of coils according to the embodiment of the present invention.

Furthermore, the plurality of coils 331 to 334 may be disposed so as to coincide with the positions of the plurality of blades 321 and 324 of the propeller 320, and may be arranged in a parallel to each other as illustrated in FIG. 4. In this case, it is possible to further increase the current inducement effect with respect to the magnetic flux density variation.

The induced current generation device 300 may additionally include an air pipe 400 which is implemented in a cylindrical shape so as to be inserted into a person's nose. In this case, air inhaled or exhaled through the person's nose passes only through the body 310 of the induced current generation device 300. The air pipe 400 may be formed of silicone.

The wearable respiration measurement apparatus having the above-described structure is operated as will be described below, and derives information on one or more of the respiration rate and the respiration amount.

First, when a person wearing the wearable respiration measurement apparatus starts inhaling, the exhalation valve plate 314 is closed by inhalation pressure caused by the inhalation, and the inhalation valve plate 313 is opened to introduce air through the inhalation path 313.

Then, the magnetized propeller 320 installed in the inhalation path 311 is rotated to induce magnetic flux density variations, and the plurality of coils 331 to 314 installed on the inner surface of the inhalation path 311 detect the magnetic flux density variations to generate induced currents.

Accordingly, it can be seen that the induced current generation period of the coils 331 to 334 coincides with the inhalation period and the induced current generated by the coils 331 to 334 is proportional to the respiration (inhalation) amount of the person wearing the wearable respiration measurement apparatus.

That is, the respiration rate and the respiration amount of the person wearing the wearable respiration measurement apparatus may be derived from the generation period of the induced current generated through the coils 331 to 334 and the induced current value.

The nose flap 200 may be implemented in such a manner as to cover only the nose, as illustrated in FIG. 1. Alternatively, the nose flap 200 may be implemented in such a manner as to cover both the nose and the mouth, as illustrated in FIG. 5.

The wearable respiration measurement apparatus according to the embodiment of the present invention measures an air flow breathed through a user's nose. Therefore, when the user breathes through his or her mouth, an error may occur, or the wearable respiration measurement apparatus may become useless. When the user becomes accustomed to wearing the wearable respiration measurement apparatus through practice, such an error may be prevented. Otherwise, a mouthpiece may be additionally provided. The mouthpiece is not provided for a specific use, but merely serves to induce the user to breathe through the nose, while the respiration is measured in a state in which the user takes the mouthpiece.

Accordingly, the mouthpiece needs to be manufactured so as to be slim by using a material which does not cause foreign body sensation.

Figure 5:
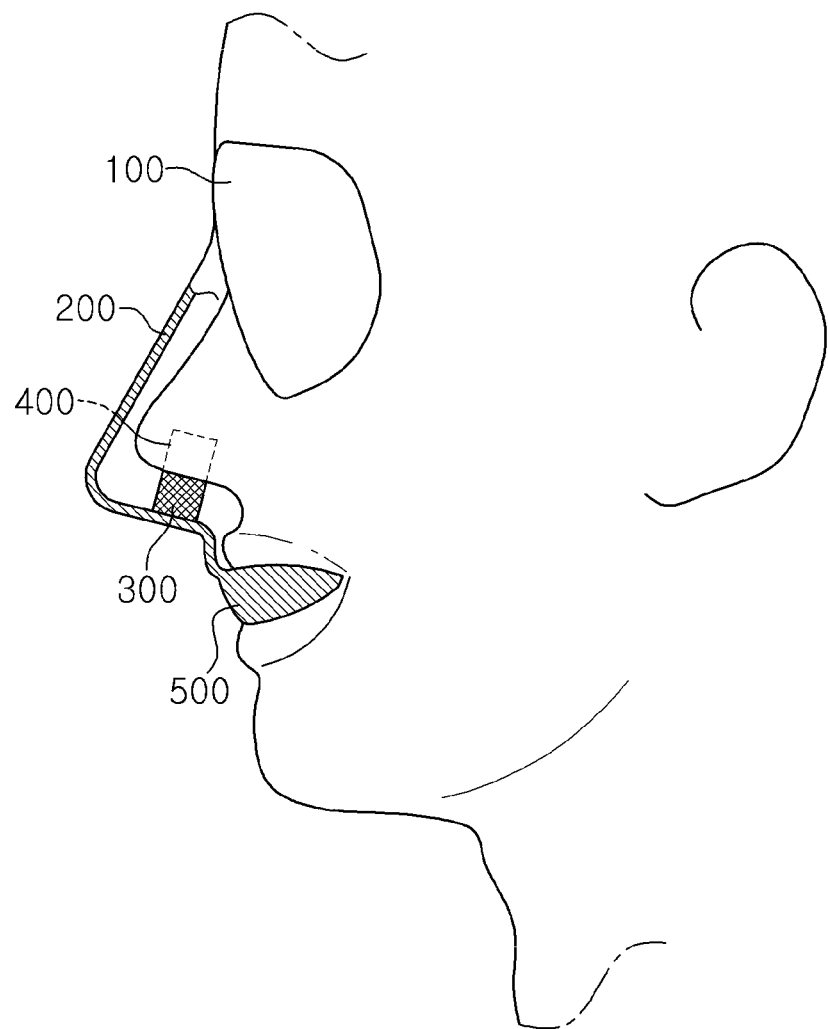
FIG. 5 is a cross-sectional view illustrating the exterior of a wearable respiration apparatus according to another embodiment of the present invention.

Referring to FIG. 5, the nose flap 200 may be designed in such a manner as to reach the mouth. In this case, the mouthpiece 500 may be integrated with the nose flap 200 so as to be positioned under the nose flap 200.

Similarly, a modified mouthpiece into which a mechanism such as the induced current generation device 300 is inserted may be provided. In this case, it is possible to detect an air flow breathed through the mouth as well as the air flow breathed through the nose. Furthermore, when a temperature sensor capable of measuring a body temperature is mounted in the mouthpiece 500, it is possible to measure the internal temperature of the mouth.

When the nose flap 200 is designed in such a manner as to reach the mouth, it may remove hot and humid feelings which may be caused when a user wears an existing mask-type respiration measurement apparatus. Therefore, the respiration measurement apparatus including the nose flap 200 designed in the above-described manner may be applied even when a user exercises strenuously. Furthermore, since the respiration measurement apparatus has a structure that is not closely attached to the skin, it may be free from sweat or stuffiness.

On the other hand, when the person wearing the wearable respiration measurement apparatus exhales, the exhalation valve plate 314 is opened and the inhalation valve plate 313 is closed by the exhalation pressure. Then, the air is discharged only through the exhalation path 312. Accordingly, the exhaled air is discharged regardless of the rotation of the propeller 320.

The wearable respiration measurement apparatus according to the embodiment of the present invention may further include a signal processing device which is attached to or inserted into any one portion of the eyeglass frame 100, for example, a temple of the eyeglass frame 100, and analyzes the induced current generated by the plurality of coils 331 to 334 to derive information on one or more of the user's respiration rate and respiration amount.

At this time, the induced current generated by the plurality of coils 331 to 334 may be transferred to the signal processing device 600 along the eyeglass frame 100. In order to reduce noise in an analog signal, the nose flap 200 may convert the analog signal into a digital signal and then transfer the converted digital signal.

Figure 6:
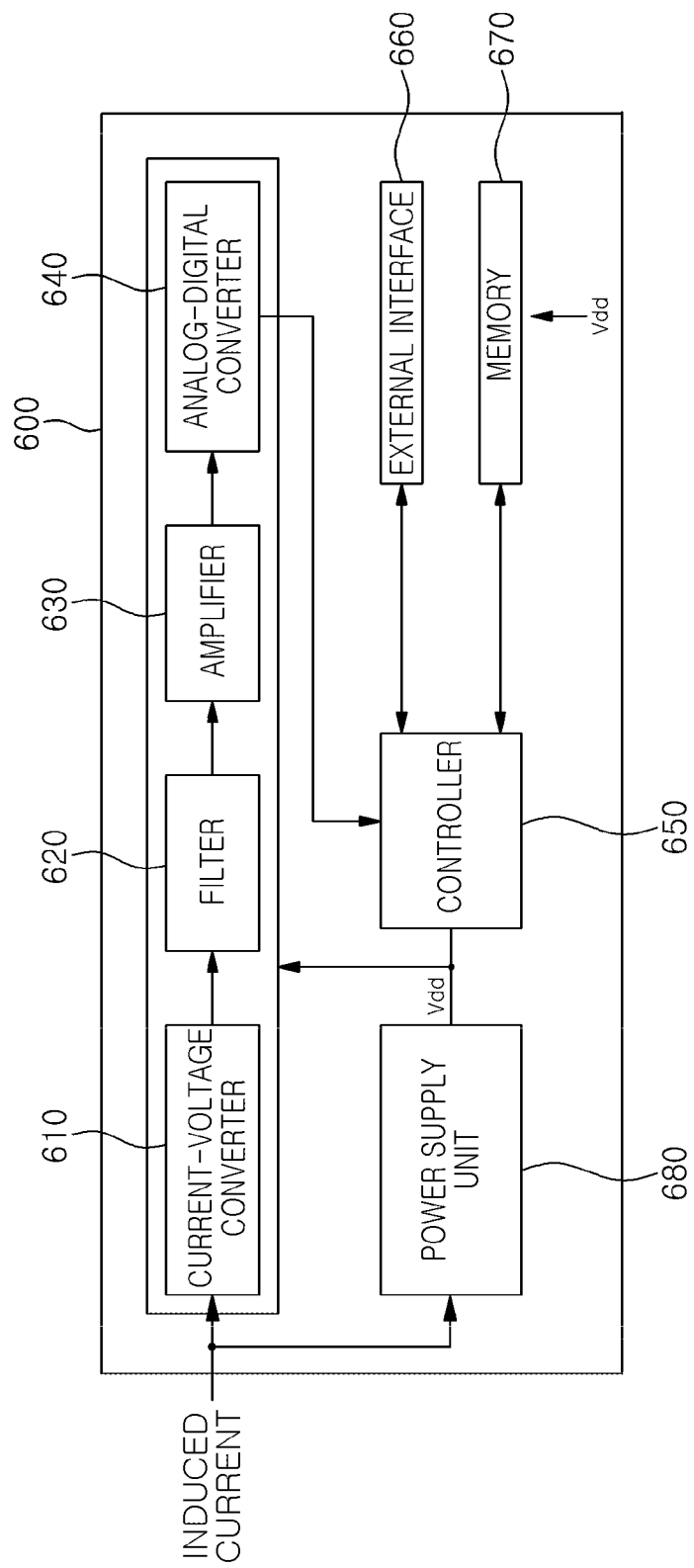
FIG. 6 is a configuration diagram of a signal processing device according to the embodiment of the present invention.

FIG. 6 is a diagram illustrating the configuration of the signal processing device according to the embodiment of the present invention.

Referring to FIG. 6, the signal processing device 600 according to the embodiment of the present invention may include a current-voltage converter 610, a filter 620, an amplifier 630, an analog-digital converter 640, a controller 650, an external interface 660, a memory 670, and a power supply unit 680. The current-voltage converter 610 converts the induced current generated by the plurality of coils 331 to 334 into a voltage. The filter 620 removes noise contained in the voltage converted by the current-voltage converter 610, in order to improve a signal characteristic. The amplifier 630 amplifies the voltage from which the noise is removed. The analog-digital amplifier 640 generates a digital signal corresponding to the voltage amplified by the amplifier 630. The controller 650 analyzes the generation pattern of the digital signal generated by the analog-digital converter 640 to calculate the respiration rate and the respiration amount. The external interface 660 provides the output of the controller 650 or information stored in the memory 670 to an external device such as a personal computer (PC), a mobile phone, or a personal digital assistant (PDA) through a wired or wireless communication scheme. The memory 670 stores the output of the controller 650. The power supply unit 680 provides power required for driving the signal processing device 600.

Figure 7:
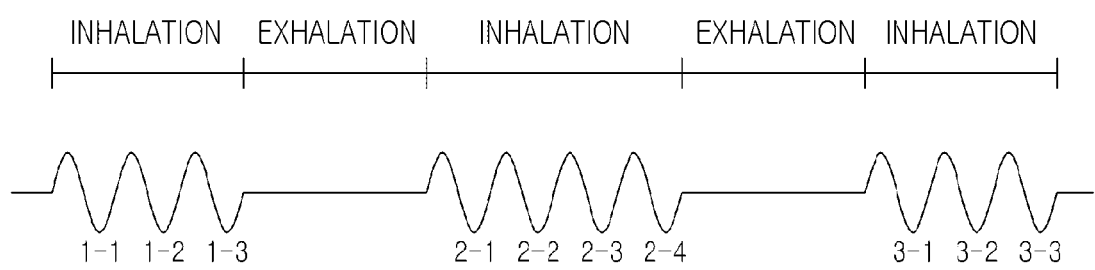
FIG. 7 is a diagram explaining a process of calculating the respiration rate and a respiration amount according to the embodiment of the present invention.

The controller 650 may analyze the waveform of the induced current to discriminate the inhalation and the exhalation. That is, referring to FIG. 7, the controller 650 may determine a period in which the induced current is generated as an inhalation generation period and determine a period in which the induced current is not generated as an exhalation generation period. Furthermore, the respiration rate may be derived from the number of inhalations and exhalations, and the respiration amount may be derived from the generated number of inhalation peaks.

The information derived from the controller 650 may be stored in the memory 670 or transmitted to a terminal such as a PC through the external interface 660.

The signal processing device 600 configured and operated in such a manner may have such a structure that is inserted into a temple of the eyeglass frame 100. Only the current-voltage converter 610, the filter 620, the amplifier 630, and the analog-digital converter 640 may be positioned in the nose flap 200, in order to generate a signal flow stronger against noise.

At this time, the body 310 of the induced current generation device 300 may be formed of a material having a signal shielding function. Then, the body 310 may have a strong characteristic against external noise.

Furthermore, since the power supply unit 680 may charge the wearable respiration measurement apparatus with the induced current, it is possible to increase the available operation time of the wearable respiration measurement apparatus. That is, since the induced currents may be collected and used as power, battery lifespan may be increased, or a battery may be recharged.

The wearable respiration measurement apparatus according to the embodiment of the present invention may acquire information related to respiration through the above-described series of processes. The wearable respiration measurement apparatus may acquire information during both daily life and exercise. Therefore, the wearable respiration measurement apparatus according to the embodiment of the present invention may be used not only for monitoring a patient having a respiratory disease, for but also estimating calories expended during exercise. When an exercise volume is measured with an acceleration signal, it is possible to increase the measurement precision for calories expended during exercise. Furthermore, it is possible to estimate a basal metabolic rate when a user is inactive, that is, when an acceleration signal is not detected. Furthermore, the wearable respiration measurement apparatus according to the embodiment of the present invention may be used for measuring calories consumed during a workout.

In the above-described embodiment, the inhalation of a user is used to calculate the respiration rate and the respiration amount. If necessary, however, the exhalation of the user may be used to calculate the respiration rate and the respiration amount. That is, the exhalation path may be housed in the inhalation path, and a propeller having a magnetic property and a plurality of coils may be installed in the exhalation path. Then, the propeller installed in the exhalation path may be rotated to calculate respiration-related information through the exhalation of the user.

Furthermore, the wearable respiration measurement apparatus according to the embodiment of the present invention may include two induced current generation devices. In this case, the wearable respiration measurement apparatus may measure an amount of air inhaled or exhaled through both nostrils, and calculate respiration-related information from the amount of air. Both of the induced current generation devices may be configured to generate induced currents based on inhalation or exhalation. Alternatively, one of the induced current generation devices may be configured to generate an induced current based on inhalation, and the other may configured to generate an induced current based on exhalation.

According to the embodiment of the present invention, the wearable respiration measurement apparatus may measure the respiration rate and the respiration amount during daily life or exercise anytime and anywhere.

The wearable respiration measurement apparatus directly measures air inhaled or exhaled through a person's nose to figure out the respiration rate and the respiration amount. Therefore, it is possible to remarkably increase measurement precision.

Furthermore, since the wearable respiration measurement apparatus may provide respiration-related information to an external device through the external interface, the wearable respiration measurement apparatus may be used for preventing or monitoring a respiratory disease. Furthermore, the respiration-related information may be used for estimating a person's calorie consumption or utilized as a parameter for measuring energy expenditure more precisely.

While the present invention has been shown and described in connection with the exemplary embodiments, it will be apparent to those skilled in the art that modifications and variations can be made without departing from the spirit and scope of the invention as defined by the appended claims.

What is claimed is:

1. A wearable respiration measurement apparatus comprising:
   an eyeglass frame including a nose flap that covers a user's nose; and
   an induced current generation device attached to the nose flap and generating an induced current corresponding to an amount of air inhaled through the user's nose,
   wherein the induced current generation device comprises:
   a body having provided therein a structure defining an exhalation path and a structure defining an inhalation path housed within the structure defining the exhalation path, the structure defining the inhalation path including an inhalation valve plate, and the structure defining the exhalation path including an exhalation valve plate;
   wherein the exhalation valve plate is provided at an upper portion of the exhalation path and is configured to be open during exhalation and closed during inhalation,
   wherein the inhalation valve plate is provided at an upper portion of the inhalation path and is configured to be open during inhalation and closed during exhalation,
   wherein the exhalation valve plate is provided over the inhalation valve plate, and
   wherein a path extends from the inhalation valve plate to the exhalation valve plate to form a hole in the exhalation valve plate so that inhaled air passes through the path and the hole.

2. The wearable respiration measurement apparatus of claim 1, wherein the induced current generation device comprises:
   a propeller installed in the inhalation path so as to be rotated by air inhaled through the inhalation path; and
   a plurality of coils installed on an inner surface of the structure defining the inhalation path, the plurality of coils generating the induced current-,
   wherein the induced current corresponds to alternating magnetic fields caused by rotation of the propeller.

3. The wearable respiration measurement apparatus of claim 2, wherein the propeller comprises a plurality of blades having a magnetic property,
   wherein the plurality of blades includes odd-numbered blades and even-numbered blades, and
   wherein the odd-numbered blades have an opposite magnetic polarity to the even-numbered blades.

4. The wearable respiration measurement apparatus of claim 2, wherein the plurality of coils includes odd-numbered coils and even-numbered coils, and
   wherein the odd-numbered coils have an opposite polarity to the even-numbered coils.

5. The wearable respiration measurement apparatus of claim 2, wherein the plurality of coils are coupled in parallel to each other.

6. The wearable respiration measurement apparatus of claim 2, wherein the body further comprises:
   a frame fixing a position of the inhalation path inside of the exhalation path and fixing a position of the propeller.

7. The wearable respiration measurement apparatus of claim 1, wherein the nose flap is implemented in such a manner as to cover only the nose or cover both the nose and the mouth.

8. The wearable respiration measurement apparatus of claim 7, further comprising a mouthpiece for inducing respiration through the nose, when the nose flap is implemented in such a manner as to cover only the nose,
   wherein the mouthpiece is separate from the eyeglass frame.

9. The wearable respiration measurement apparatus of claim 8, wherein the mouthpiece comprises a temperature sensor mounted thereon.

10. The wearable respiration measurement apparatus of claim 7, further comprising a mouthpiece for inducing respiration through the nose, when the nose flap is implemented in such a manner as to cover both the nose and the mouth,
    wherein the mouthpiece is coupled to the eyeglass frame and positioned under the nose flap.

11. The wearable respiration measurement apparatus of claim 10, wherein the mouthpiece comprises a temperature sensor mounted thereon.

12. The wearable respiration measurement apparatus of claim 1, further comprising a signal processing device coupled to, or inserted into, the eyeglass frame and generating respiration-related information corresponding to the induced current.

13. The wearable respiration measurement apparatus of claim 12, wherein the signal processing device comprises:
    a current-voltage converter configured to convert the induced current into a voltage;
    a filter configured to remove noise in the voltage;
    an amplifier configured to amplify the filtered voltage;
    an analog-digital converter configured to generate a digital signal corresponding to the amplified voltage; and
    a controller configured to analyze a generation pattern of the digital signal to calculate information including any of a respiration rate and a respiration amount.

14. The wearable respiration measurement apparatus of claim 13, wherein the signal processing device further comprises:
    a memory configured to store an output of the controller; and
    an external interface configured to provide an output of the controller to an external device through a wired or wireless communication scheme.

15. The wearable respiration measurement apparatus of claim 13, wherein the signal processing device further comprises a power supply unit configured to provide power to drive the signal processing device.

16. The wearable respiration measurement apparatus of claim 15, wherein the power supply unit is configured to charge the wearable respiration measurement apparatus with the induced current.

17. The wearable respiration measurement apparatus of claim 1, wherein the induced current generator is positioned on the nose flap and includes an air pipe to align the body of the wearable respiration measurement apparatus with a nostril of the user's nose.

* * * * *